(12) United States Patent
Hunt et al.

(10) Patent No.: US 8,696,665 B2
(45) Date of Patent: Apr. 15, 2014

(54) SURGICAL CUTTING AND SEALING INSTRUMENT WITH REDUCED FIRING FORCE

(75) Inventors: John V. Hunt, Cincinnati, OH (US); Robert J. Laird, Morrow, OH (US); Omar J. Vakharia, Cincinnati, OH (US); Richard W. Timm, Cincinnati, OH (US); Gavin M. Monson, Oxford, OH (US); Suzanne E. Thompson, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 986 days.

(21) Appl. No.: 12/732,992

(22) Filed: Mar. 26, 2010

(65) Prior Publication Data
US 2011/0238065 A1  Sep. 29, 2011

(51) Int. Cl.
*A61B 18/14* (2006.01)
*A61B 17/28* (2006.01)

(52) U.S. Cl.
USPC ............... 606/51; 606/52; 606/205; 606/206; 606/207

(58) Field of Classification Search
USPC ..................... 606/50–52, 205–207
See application file for complete search history.

(56) References Cited

U.S. PATENT DOCUMENTS

| | | | |
|---|---|---|---|
| 3,580,841 A | 5/1971 | Cadotte et al. | |
| 3,703,651 A | 11/1972 | Blowers | |
| 4,058,126 A | 11/1977 | Leveen | |
| 4,237,441 A | 12/1980 | van Konynenburg et al. | |
| 4,304,987 A | 12/1981 | van Konynenburg | |
| 4,545,926 A | 10/1985 | Fouts, Jr. et al. | |
| 4,849,133 A | 7/1989 | Yoshida et al. | |
| 4,910,389 A | 3/1990 | Sherman et al. | |
| 5,104,025 A | 4/1992 | Main et al. | |
| 5,106,538 A | 4/1992 | Barma et al. | |

(Continued)

FOREIGN PATENT DOCUMENTS

| | | |
|---|---|---|
| DE | 20004812 U1 | 9/2000 |
| EP | 0705571 A1 | 4/1996 |
| WO | WO 96/35382 A1 | 11/1996 |
| WO | WO 03/030708 A2 | 4/2003 |

(Continued)

OTHER PUBLICATIONS

International Search Report for PCT/US2011/029560, Jul. 1, 2011 (5 pages).

(Continued)

*Primary Examiner* — Michael Peffley
*Assistant Examiner* — Khadijeh Vahdat

(57) ABSTRACT

A surgical instrument is provided that can comprise and end effector including two jaws and a cutting member configured to move between the jaws. In at least one embodiment, one or both of the jaws may be flexible, such that a jaw is configured to flex when gripping tissue. Further, at least one of the jaws may include a thin cross-sectional area such that the jaw flexes when gripping tissue. Additionally, in at least one embodiment, one or more compression elements may extend from the cutting member and may be configured to cause the jaws to close when the cutting member is advanced. The compression elements may comprise a roller and/or a low-friction material. Moreover, in at least one embodiment, one or both of the jaws may be precurved, away from the cutting member's longitudinal axis. Accordingly, in various embodiments, the overall force required to advance the cutting member and/or close the jaws may be reduced.

23 Claims, 7 Drawing Sheets

(56) References Cited

U.S. PATENT DOCUMENTS

| | | |
|---|---|---|
| 5,108,383 A | 4/1992 | White |
| 5,205,459 A | 4/1993 | Brinkerhoff et al. |
| 5,285,945 A | 2/1994 | Brinkerhoff et al. |
| 5,309,927 A | 5/1994 | Welch |
| 5,318,589 A * | 6/1994 | Lichtman .................... 606/205 |
| 5,387,207 A | 2/1995 | Dyer et al. |
| 5,403,312 A | 4/1995 | Yates et al. |
| 5,428,504 A | 6/1995 | Bhatla |
| 5,504,650 A | 4/1996 | Katsui et al. |
| 5,511,556 A | 4/1996 | DeSantis |
| 5,558,671 A | 9/1996 | Yates |
| 5,563,179 A | 10/1996 | Stone et al. |
| 5,599,350 A | 2/1997 | Schulze et al. |
| 5,624,452 A | 4/1997 | Yates |
| 5,647,871 A | 7/1997 | Levine et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,880,668 A | 3/1999 | Hall |
| 6,003,517 A | 12/1999 | Sheffield et al. |
| 6,063,098 A | 5/2000 | Houser et al. |
| 6,074,389 A | 6/2000 | Levine et al. |
| 6,099,483 A * | 8/2000 | Palmer et al. .................. 600/564 |
| 6,292,700 B1 | 9/2001 | Morrison et al. |
| 6,340,878 B1 | 1/2002 | Oglesbee |
| 6,500,176 B1 | 12/2002 | Truckai et al. |
| 6,503,248 B1 | 1/2003 | Levine |
| 6,514,252 B2 | 2/2003 | Nezhat et al. |
| 6,533,784 B2 | 3/2003 | Truckai et al. |
| 6,575,969 B1 | 6/2003 | Rittman, III et al. |
| 6,589,200 B1 | 7/2003 | Schwemberger et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,860,880 B2 | 3/2005 | Treat et al. |
| 6,905,497 B2 | 6/2005 | Truckai et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,371,227 B2 | 5/2008 | Zeiner |
| 7,381,209 B2 | 6/2008 | Truckai et al. |
| 7,404,508 B2 | 7/2008 | Smith et al. |
| 7,435,582 B2 | 10/2008 | Zimmermann et al. |
| 7,464,846 B2 | 12/2008 | Shelton, IV et al. |
| 7,510,107 B2 | 3/2009 | Timm et al. |
| 7,513,025 B2 | 4/2009 | Fischer |
| 7,550,216 B2 | 6/2009 | Ofer et al. |
| 7,588,176 B2 | 9/2009 | Timm et al. |
| 7,641,671 B2 | 1/2010 | Crainich |
| 7,658,311 B2 | 2/2010 | Boudreaux |
| 7,665,647 B2 | 2/2010 | Shelton, IV et al. |
| 7,708,751 B2 | 5/2010 | Hughes et al. |
| 7,753,904 B2 | 7/2010 | Shelton, IV et al. |
| 7,784,663 B2 | 8/2010 | Shelton, IV |
| 7,819,298 B2 | 10/2010 | Hall et al. |
| 7,832,612 B2 | 11/2010 | Baxter, III et al. |
| 7,879,070 B2 | 2/2011 | Ortiz et al. |
| 7,931,649 B2 | 4/2011 | Couture et al. |
| 2002/0115997 A1 * | 8/2002 | Truckai et al. .................. 606/51 |
| 2003/0114851 A1 * | 6/2003 | Truckai et al. .................. 606/51 |
| 2003/0199870 A1 * | 10/2003 | Truckai et al. .................. 606/51 |
| 2004/0193150 A1 | 9/2004 | Sharkey et al. |
| 2004/0232196 A1 | 11/2004 | Shelton, IV et al. |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0206140 A1 | 8/2009 | Scheib et al. |
| 2009/0209979 A1 | 8/2009 | Yates et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036405 A1 | 2/2010 | Giordano et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2011/0087208 A1 | 4/2011 | Boudreaux et al. |
| 2011/0087209 A1 | 4/2011 | Boudreaux et al. |
| 2011/0087218 A1 | 4/2011 | Boudreaux et al. |
| 2011/0087219 A1 | 4/2011 | Boudreaux et al. |
| 2011/0087220 A1 | 4/2011 | Felder et al. |

FOREIGN PATENT DOCUMENTS

| | | |
|---|---|---|
| WO | WO 03/068046 A2 | 8/2003 |
| WO | WO 2005/052959 A2 | 6/2005 |

OTHER PUBLICATIONS

Kurt Gieck & Reiner Gieck, *Engineering Formulas* § Z.7 (7th ed. 1997).

(56) References Cited

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

National Semiconductors Temperature Sensor Handbook—http://www.national.com/appinfo/tempsensors/files/temphb.pdf; accessed online: Apr. 1, 2011.

U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.

\* cited by examiner

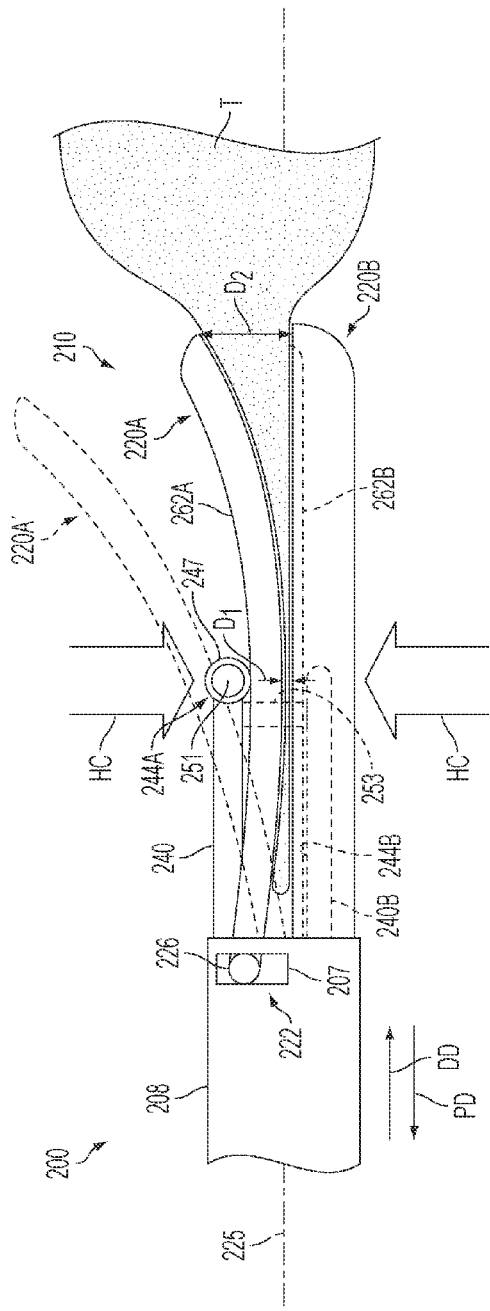
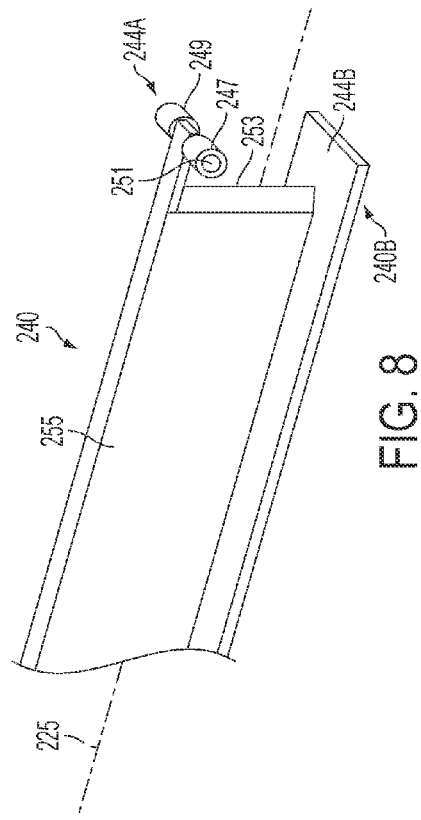
FIG. 7
FIG. 8

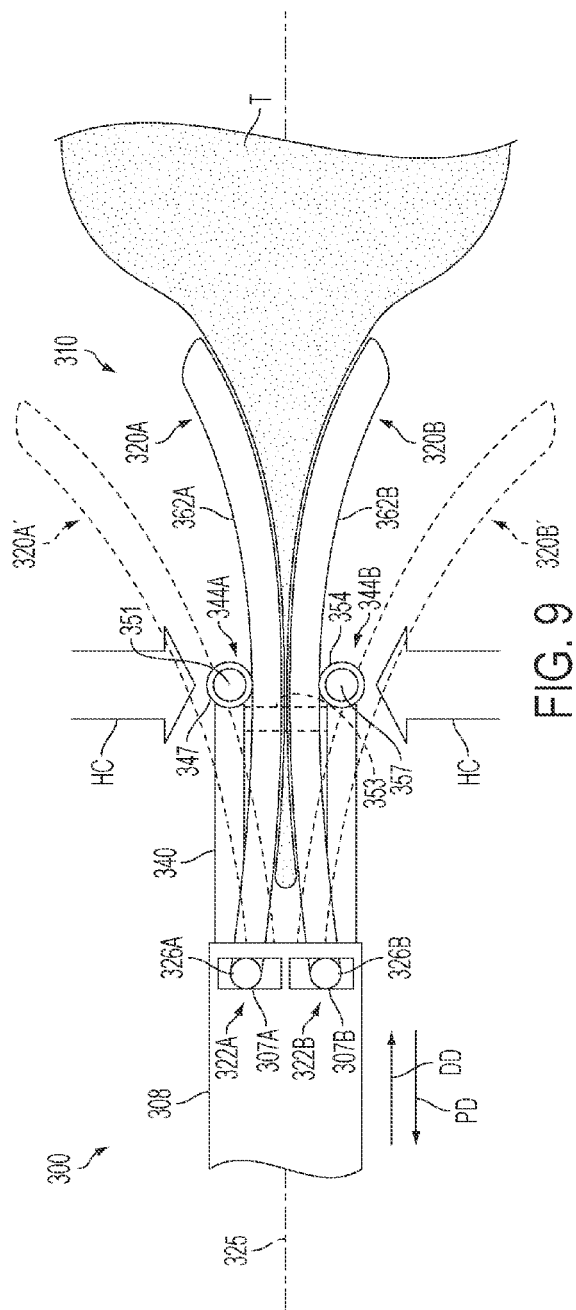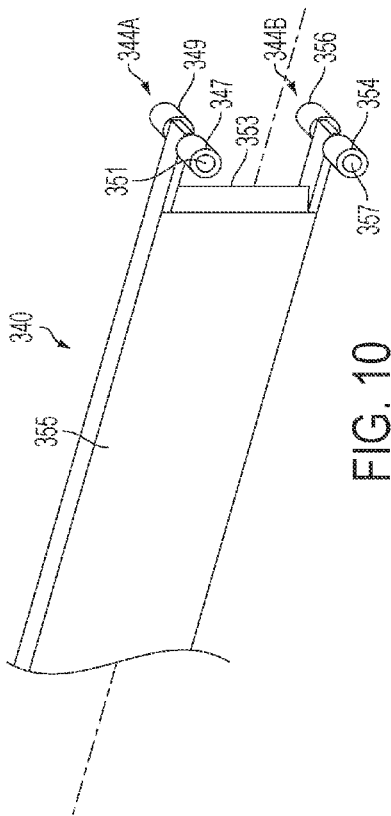

SURGICAL CUTTING AND SEALING INSTRUMENT WITH REDUCED FIRING FORCE

BACKGROUND

The present disclosure is directed to medical devices and methods, and, more particularly, to electrosurgical instruments and methods for sealing and transecting tissue.

In various circumstances, a surgical instrument can be configured to apply energy to tissue in order to treat and/or destroy the tissue. In certain circumstances, a surgical instrument can comprise one or more electrodes which can be positioned against and/or positioned relative to the tissue such that electrical current can flow from one electrode, through the tissue, and to the other electrode. The surgical instrument can comprise an electrical input, a supply conductor electrically coupled with the electrodes, and/or a return conductor which can be configured to allow current to flow from the electrical input, through the supply conductor, through the electrodes and the tissue, and then through the return conductor to an electrical output, for example. In various circumstances, heat can be generated by the current flowing through the tissue, wherein the heat can cause one or more hemostatic seals to form within the tissue and/or between tissues. Such embodiments may be particularly useful for sealing blood vessels, for example. The surgical instrument can also comprise a cutting member that can be moved relative to the tissue and the electrodes in order to transect the tissue.

By way of example, energy applied by a surgical instrument may be in the form of radio frequency ("RF") energy. RF energy is a form of electrical energy that may be in the frequency range of 300 kilohertz (kHz) to 1 megahertz (MHz). In application, RF surgical instruments transmit low frequency radio waves through electrodes, which cause ionic agitation, or friction, increasing the temperature of the tissue. Since a sharp boundary is created between the affected tissue and that surrounding it, surgeons can operate with a high level of precision and control, without much sacrifice to the adjacent normal tissue. The low operating temperatures of RF energy enables surgeons to remove, shrink or sculpt soft tissue while simultaneously sealing blood vessels. RF energy works particularly well on connective tissue, which is primarily comprised of collagen and shrinks when contacted by heat.

Further, in various open and laparoscopic surgeries, it may be necessary to coagulate, seal or fuse tissues. One means of sealing tissue relies upon the application of electrical energy to tissue captured within an end effector of a surgical instrument in order to cause thermal effects within the tissue. Various mono-polar and bi-polar RF jaw structures have been developed for such purposes. In general, the delivery of RF energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds," together as the proteins renature. As the treated region heals over time, this biological "weld" may be reabsorbed by the body's wound healing process.

In certain arrangements of a bi-polar radiofrequency (RF) jaw, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate the present field and should not be taken as a disavowal of claim scope.

SUMMARY

In various embodiments, a surgical instrument is provided. In at least one embodiment, the surgical instrument can comprise an end effector comprising a first flexible jaw defining a longitudinal axis and a channel, a second jaw, a cutting member including a distal end, and at least one compression element extending from the cutting member. Further, in these embodiments, the first jaw and the second jaw can be operably coupled together. Additionally, in these embodiments, in these embodiments, the cutting member can be sized and configured to fit at least partially within the channel and the cutting member can be configured to translate along the channel between a retracted position and a fully advanced position. Moreover, in these embodiments, the first flexible jaw can have a thickness less than or equal to about 1.3 mm in a direction perpendicular to the longitudinal axis and at a plane that transects the channel at the distal end of the cutting member when the cutting member is between the retracted position and the fully advanced position. Also, in these embodiments, the at least one compression element can be configured to cause the first flexible jaw to rotate with respect to the second jaw from an open position to a closed position when the cutting member translates with respect to the first flexible jaw beyond the retracted position.

In at least one embodiment, a surgical instrument is provided that can comprise an end effector comprising a first jaw, a second jaw, a cutting member configured to translate with respect to the first jaw and the second jaw, and at least one compression element extending from the cutting member. In these embodiments, the first jaw and the second jaw can be operably coupled together. Further, in these embodiments, the at least one compression element can be configured to contact the first jaw such that the first jaw rotates with respect to the second jaw when the cutting member translates with respect to the first jaw. Moreover, in these embodiments, the at least one compression element can comprise one or both of a roller and a low-friction material. Additionally, in these embodiments, the static coefficient of friction between the low-friction material and the first jaw can be less than or equal to about 0.10.

In at least one embodiment, a surgical instrument is provided that can comprise an end effector comprising a first jaw, a second jaw, a cutting member configured to translate with respect to the first jaw between a retracted position and a fully advanced position, and at least one compression element extending from the cutting member. In these embodiments, the first jaw and the second jaw can be operably coupled together. Further, in these embodiments, the cutting member can define a longitudinal axis. Additionally, the at least one compression element can be configured to contact the first jaw such that the first jaw rotates with respect to the second jaw between an open position and a closed position when the cutting member translates with respect to the first jaw. Moreover, the first jaw can be precurved such that the first jaw curves away from the longitudinal axis when the first jaw is in the open position and no external load is applied to the first jaw.

The foregoing discussion should not be taken as a disavowal of claim scope.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 7 is a schematic diagram of a side view of an end effector of a surgical instrument gripping tissue according to a non-limiting embodiment; a cutting member is shown in a partially advanced position.

FIG. 8 is a perspective view of a distal portion of the cutting member of FIG. 7.

FIG. 9 is a schematic diagram of a side view of an end effector of a surgical instrument gripping tissue according to a non-limiting embodiment; a cutting member is shown in a partially advanced position.

FIG. 10 is a perspective view of a distal portion of the cutting member of FIG. 9.

Figure 1:
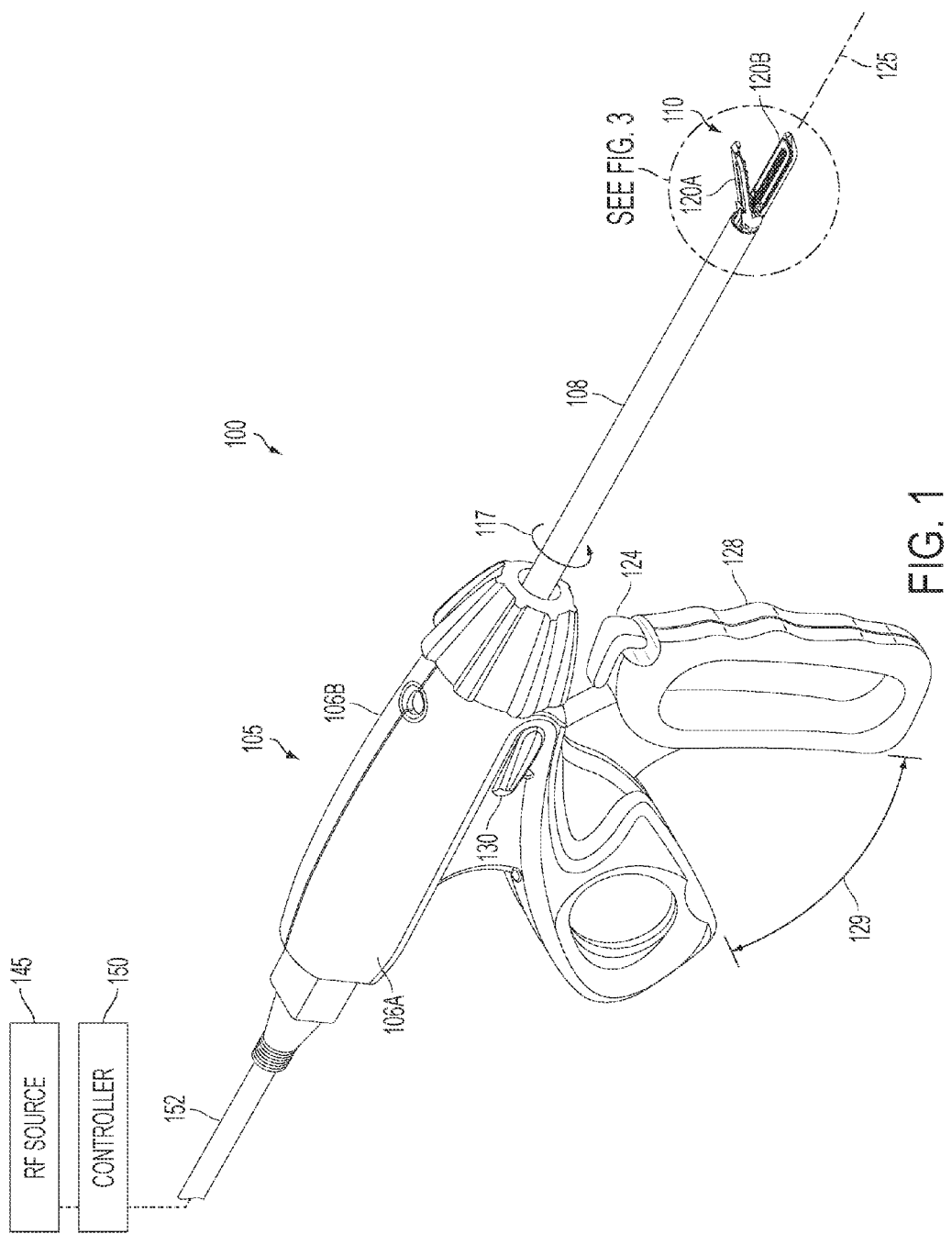
FIG. 1 is a perspective view of a surgical instrument according to a non-limiting embodiment.

Corresponding reference characters indicate corresponding parts throughout the several views. The exemplifications set out herein illustrate various embodiments, in one or more forms, and such exemplifications are not to be construed as limiting the scope of the claims in any manner.

DETAILED DESCRIPTION

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

Various embodiments of systems and methods relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

A surgical instrument can be configured to supply energy, such as electrical energy and/or heat energy, to the tissue of a patient. For example, various embodiments disclosed herein provide electrosurgical jaw structures adapted for transecting captured tissue between the jaws and for contemporaneously welding the captured tissue margins with controlled application of RF energy. In more detail, in various embodiments, referring now to FIG. 1, an electrosurgical instrument 100 is shown. Surgical or electrosurgical instrument 100 can comprise a proximal handle 105, a distal working end or end effector 110 and an introducer or elongate shaft 108 disposed in-between. End effector 110 may comprise a set of openable-closeable jaws with straight or curved jaws—an upper first jaw 120A and a lower second jaw 120B. First jaw 120A and second jaw 120B may each comprise an elongate slot or channel 142A and 142B (see FIG. 3), respectively, disposed outwardly along their respective middle portions. First jaw 120A and second jaw 120B may be coupled to an electrical source or RF source 145 and a controller 150 through electrical leads in cable 152. Controller 150 may be used to activate electrical source 145.

Figure 2:
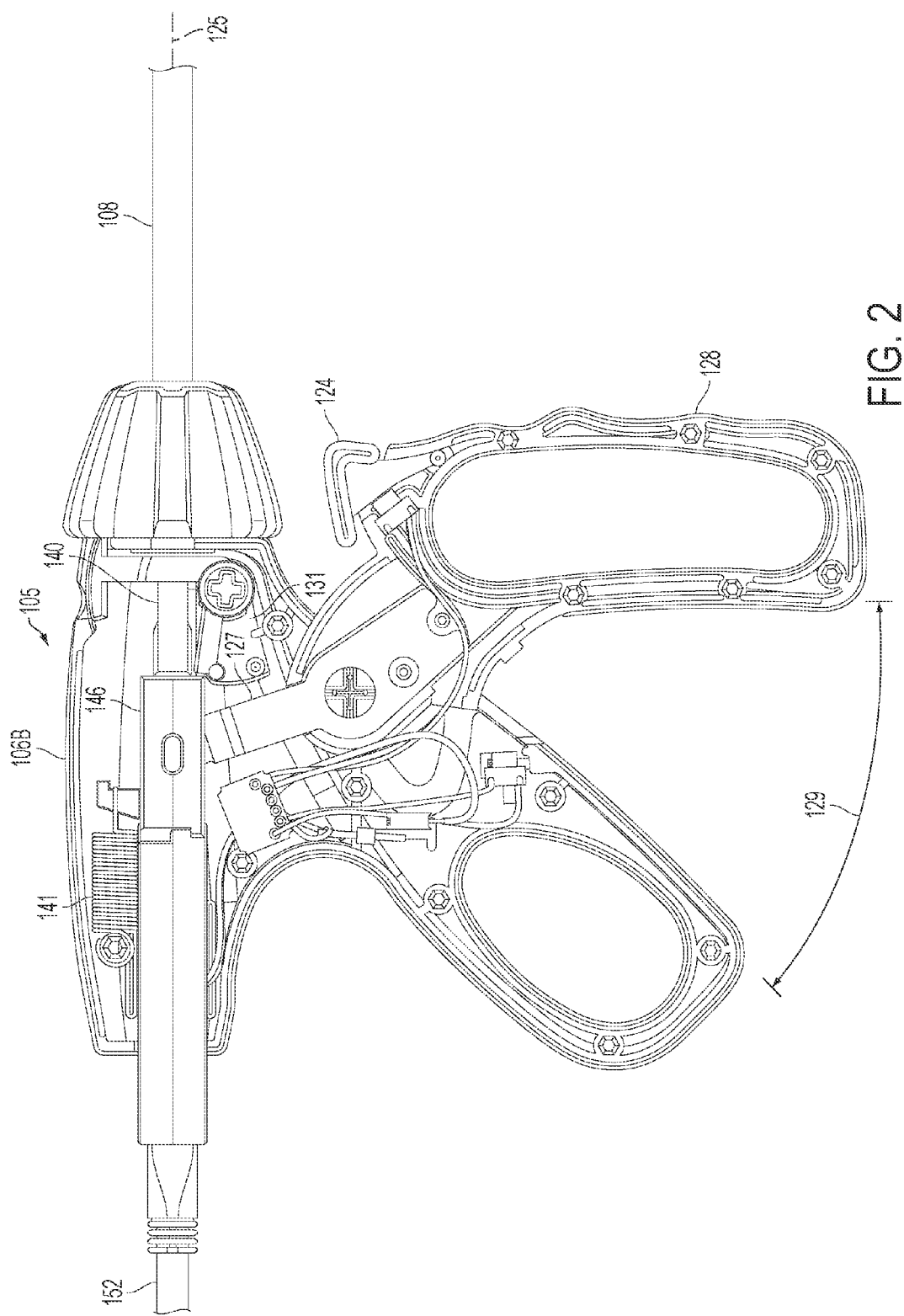
FIG. 2 is a side view of a handle of the surgical instrument of FIG. 1 with a half of a handle body removed to illustrate some of the components therein.

Moving now to FIG. 2, a side view of the handle 105 is shown with half of a first handle body 106A (see FIG. 1) removed to illustrate some of the components within second handle body 106B. Handle 105 may comprise a lever arm 128 which may be pulled along a path 129. Lever arm 128 may be coupled to a movable cutting member 140 disposed within elongate shaft 108 by a shuttle 146 operably engaged to an extension 127 of lever arm 128. The shuttle 146 may further be connected to a biasing device, such as spring 141, which may also be connected to the second handle body 106B, to bias the shuttle 146 and thus the cutting member 140 in a proximal direction, thereby urging the jaws 120A and 120B to an open position as seen in FIG. 1. Also, referring to FIGS. 1 and 2, a locking member 131 (see FIG. 2) may be moved by a locking switch 130 (see FIG. 1) between a locked position, where the shuttle 146 is substantially prevented from moving distally as illustrated, and an unlocked position, where the shuttle 146 may be allowed to freely move in the distal direction, toward the elongate shaft 108. The handle 105 can be any type of pistol-grip or other type of handle known in the art that is configured to carry actuator levers, triggers or sliders for actuating the first jaw 120A and second jaw 120B. Elongate shaft 108 may have a cylindrical or rectangular cross-section and can comprise a thin-wall tubular sleeve that extends from handle 105. Elongate shaft 108 may include a bore extending therethrough for carrying actuator mechanisms, for example, cutting member 140, for actuating the jaws and for carrying electrical leads for delivery of electrical energy to electrosurgical components of end effector 110.

End effector 110 may be adapted for capturing, welding and transecting tissue. First jaw 120A and second jaw 120B may close to thereby capture or engage tissue about a longitudinal axis 125 defined by cutting member 140. First jaw 120A and second jaw 120B may also apply compression to the tissue. Elongate shaft 108, along with first jaw 120A and second jaw 120B, can be rotated a full 360° degrees, as shown by arrow 117, relative to handle 105 through, for example, a rotary triple contact. First jaw 120A and second jaw 120B can remain openable and/or closeable while rotated.

Figure 3:
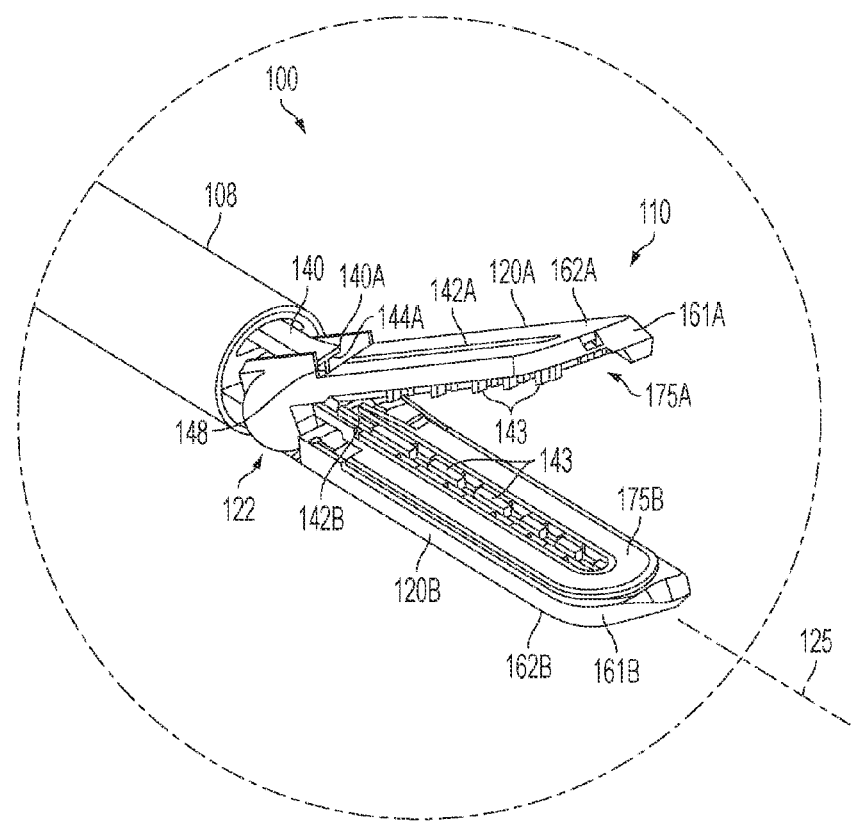
FIG. 3 is a perspective view of an end effector of the surgical instrument of FIG. 1 illustrated in an open configuration; the distal end of a cutting member is illustrated in a retracted position.
Figure 4:
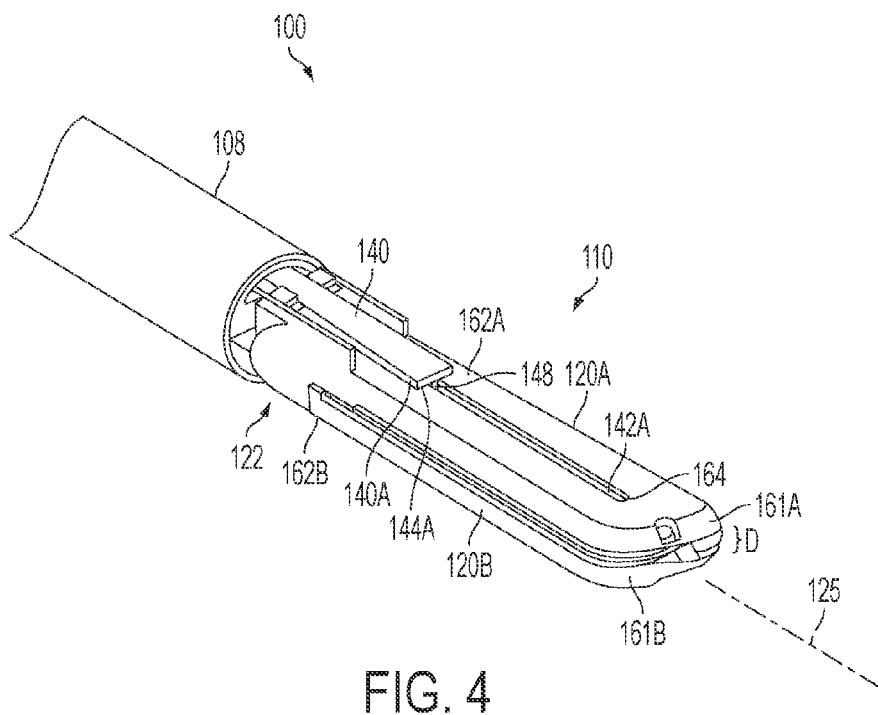
FIG. 4 is a perspective view of the end effector of the surgical instrument of FIG. 1 illustrated in a closed configuration; the distal end of the cutting member is illustrated in a partially advanced position.

FIGS. 3 and 4 illustrate perspective views of end effector 110. FIG. 3 shows end effector 110 in an open configuration and FIG. 4 shows end effector 110 in a closed configuration. As noted above, the end effector 110 may comprise the upper first jaw 120A and the lower second jaw 120B. Further, the first jaw 120A and second jaw 120B may each have tissue-gripping elements, such as teeth 143, disposed on the inner portions of first jaw 120A and second jaw 120B. First jaw 120A may comprise an upper first jaw body 161A with an upper first outward-facing surface 162A and an upper first energy delivery surface 175A. Second jaw 120B may comprise a lower second jaw body 161B with a lower second outward-facing surface 162B and a lower second energy delivery surface 175B. First energy delivery surface 175A and second energy delivery surface 175B may both extend in a "U" shape about the distal end of end effector 110.

Figure 5:
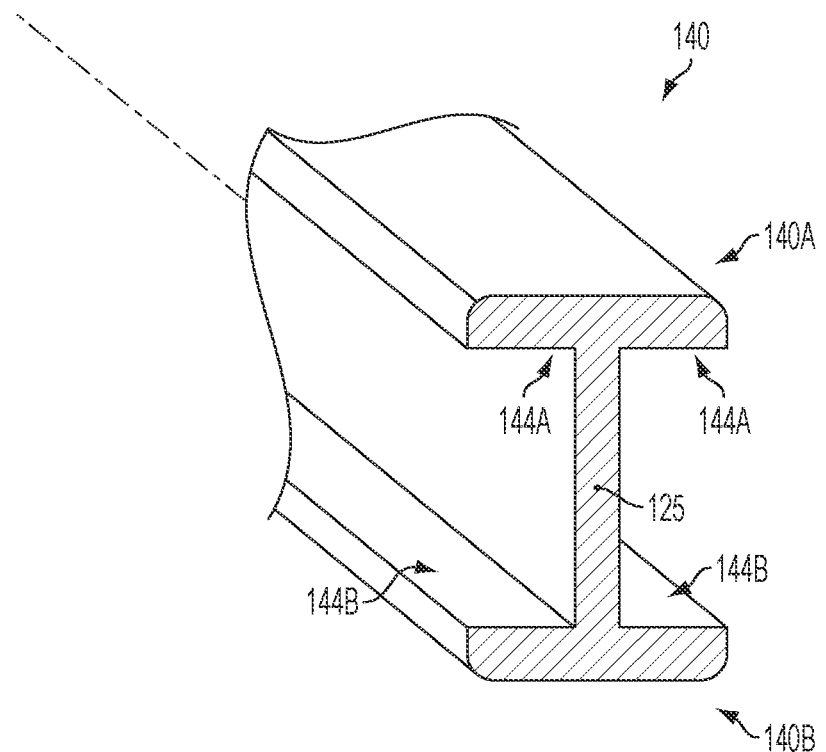
FIG. 5 is a perspective sectional view of a portion of a cutting member of the surgical instrument of FIG. 1; the cutting member is shown at least partially shaped like an I-beam.

Referring briefly now to FIG. 5, a portion of cutting member 140 is shown. The lever arm 128 of handle 105, see FIG. 2, may be adapted to actuate cutting member 140 which also functions as a jaw-closing mechanism. For example, cutting member 140 may be urged distally as lever arm 128 is pulled proximally along path 129 via shuttle 146, seen in FIG. 2 and discussed above. The cutting member 140 may comprise one or several pieces, but in any event, may be movable or translatable with respect to the elongate shaft 108 and/or jaws 120A, 120B. Also, in at least one embodiment, the cutting member 140 may be made of 17-4 precipitation hardened stainless steel. The distal end of cutting member 140 may comprise a flanged "I"-beam configured to slide within channels 142A and 142B in jaws 120A and 120B. Cutting member 140 may slide within channels 142A, 142B to open and close first jaw 120A and second jaw 120B. The distal end of cutting member 140 may also comprise upper flange or "c"-shaped portion 140A and lower flange or "c"-shaped portion 140B. The flanges 140A and 140B respectively define inner cam surfaces 144A and 144B for engaging outward facing surfaces of first jaw 120A and second jaw 120B. The opening-closing of jaws 120A and 120B can apply very high compressive forces on tissue using cam mechanisms which may include reciprocating "I-beam" cutting member 140 and the outward facing surfaces 162A, 162B of jaws 120A, 120B.

More specifically, referring now to FIGS. 3-5, collectively, inner cam surfaces 144A and 144B of the distal end of cutting member 140 may be adapted to slidably engage first outward-facing surface 162A and second outward-facing surface 162B of first jaw 120A and second jaw 120B, respectively. Channel 142A within first jaw 120A and channel 142B within second jaw 120B may be sized and configured to accommodate the movement of cutting member 140, which may comprise a tissue-cutting element, for example, a sharp distal edge. FIG. 4, for example, shows the distal end of cutting member 140 advanced at least partially through channels 142A and 142B (see FIG. 3). The advancement of cutting member 140 can close end effector 110 from the open configuration shown in FIG. 3. In the closed position shown by FIG. 4, upper first jaw 120A and lower second jaw 120B define a gap or dimension D between the first energy delivery surface 175A and second energy delivery surface 175B of first jaw 120A and second jaw 120B, respectively. Dimension D equals from about 0.0005" to about 0.005" and preferably between about 0.001" to about 0.002". Also, the edges of first energy delivery surface 175A and second energy delivery surface 175B may be rounded to prevent the dissection of tissue.

Referring now to FIGS. 1 and 3, end effector 110 may be coupled to electrical source 145 and controller 150. First energy delivery surface 175A and second energy delivery surface 175B may likewise each be coupled to electrical source 145 and controller 150. First energy delivery surface 175A and second energy delivery surface 175B may be configured to contact tissue and delivery electrosurgical energy to engaged tissue which is adapted to seal or weld the tissue. Controller 150 can regulate the electrical energy delivered by electrical source 145 which in turn delivers electrosurgical energy to first energy-delivery surface 175A and second energy-delivery surface 175B. The energy delivery may be initiated by an activation button 124 operably engaged with lever arm 128 and in electrically communication with controller 150 via cable 152. As mentioned above, the electrosurgical energy delivered by electrical source 145 may comprise radiofrequency (RF) energy. Further, the opposing first and second energy delivery surfaces 175A and 175B may carry variable resistive positive temperature coefficient (PTC) bodies that are coupled to electrical source 145 and controller 150. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,381,209; 7,311,709; 7,220,951; 7,189,233; 7,186,253; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

In at least one embodiment, one or both of the jaws 120A, 120B may be flexible, such that one of the jaws is configured to flex when gripping tissue. In at least one embodiment, referring now to FIGS. 3 and 4, the surgical instrument 100 may comprise elongate shaft 108 and end effector 110 which may be coupled together as described above. The end effector may further comprise first jaw 120A, second jaw 120B, and cutting member 140. The first jaw 120A, as will be discussed below, may be flexible. Further, the first and second jaws 120A and 120B may be pivotably coupled together at hinge portion 122. The first flexible jaw 120A may be also define channel 142A. The cutting member 140 may be sized and configured to fit at least partially within the channel 142A. The cutting member 140 may also be configured to translate along the channel 142A, as described above, between a retracted position and a fully advanced position. The retracted position can be seen in FIG. 3, where the jaws 120A, 120B are in an open position and a distal end 148 of the cutting member 140 is positioned proximal to the upper outward-facing surface 162A. The fully advanced position, while not shown, occurs when the distal end 148 of the cutting member 140 is advanced to a distal end 164 of channel 142A and the jaws are in a closed position, see FIG. 4.

The end effector 110 may further include at least one compression element extending from the cutting member 140, such as inner cam surface 144A and/or 144B of flanges 140A and 140B, see FIG. 5. Further, as described above, the compression element(s), or cam surfaces 144A and/or 144B, may be configured to cause the first flexible jaw 120A to rotate with respect to the second jaw 120B from the open position (see FIG. 3) to a closed position (see FIG. 4) when the cutting member 140 translates with respect to the first flexible jaw 120A beyond the retracted position. For example, FIG. 4, as mentioned above, shows the distal end 148 of the cutting member 140 in a partially advanced position, that is, beyond the retracted position seen in FIG. 3, but before the fully advanced position, described above. As seen in FIG. 4, the compression element(s), or inner cam surface 144A of flange 140A, extending from the cutting member 140, are in contact with the upper outward-facing surface 162A, see FIG. 5, for example, thereby holding the first flexible jaw 120A in the closed position as seen in FIG. 4.

Figure 6:
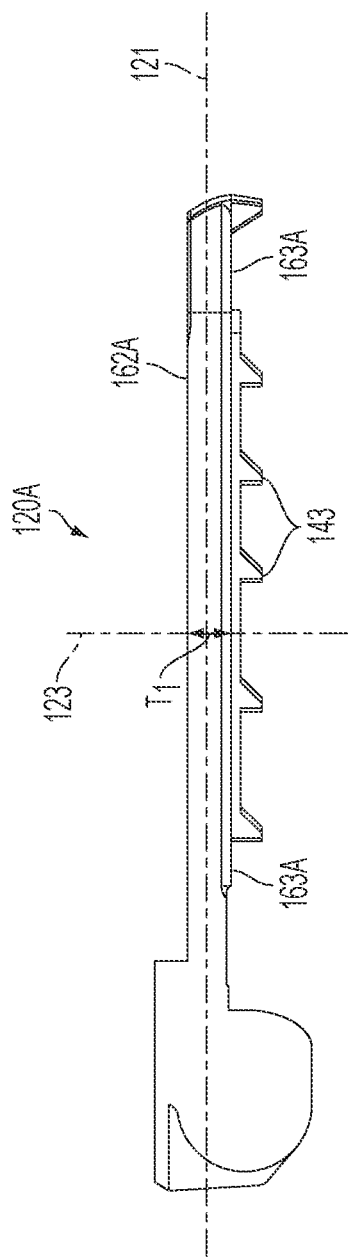
FIG. 6 is a side view of a jaw of the end effector of the surgical instrument of FIG. 1.

In at least one embodiment, the first flexible jaw 120A may be configured to flex when gripping an object, such as tissue, as follows. Referring now to FIG. 6, a side view of the first flexible jaw 120A is shown isolated from other components of the surgical instrument. Referring now to FIGS. 4 and 6, the jaw 120A may define a longitudinal axis 121 and may have a thickness T1 less than or equal to about 1.3 mm in a direction perpendicular to the longitudinal axis 121 and at plane 123 that transects the channel 142A at the distal end of the cutting member 140 when the cutting member 140 is between the retracted position and the fully advanced position, an example of which is shown in FIG. 4. The thickness T1 may be defined between a bottom surface 163A and upper surface 162A of the jaw 120A. Further, the thickness T1 may be greater than or equal to about 0.5 mm. In one embodiment, the thickness T1 may be about 1.15 mm. In any event, the width of the first flexible jaw 120A, as measured along a direction perpendicular to the plane of the page of FIG. 6, may be between and including about 2 mm to about 15 mm and the jaw 120A may be made of heat-treated stainless steel, for example. Thus, the second moment of area of the jaw 120A may be reduced over a thicker jaw having the same width. Accordingly, in such embodiments the jaw 120A may be configured to bend or flex when gripping tissue, thereby reducing the amount of force required to be applied by a user at lever arm 128, see FIG. 1, when gripping and/or cutting tissue with end effector 110, as compared to surgical instruments with jaws that are configured to be rigid and remain straight while gripping and/or cutting tissue. As used herein, the amount of force required to close the jaws 120A and 120B and/or advance the cutting member 140 therethrough is referred to as the "firing force," and the action of closing the jaws 120A and 120B and/or advancing the cutting member 140 with respect to the jaws 120A and 120B is referred to as the act of "firing" the surgical instrument 100. As will be appreciated, the amount of flex present in the first jaw 120A when firing the cutting member 140 may vary depending on where the compression element(s), or inner cam surface 144A, is in relation to channel 142A (see FIG. 4) and upper outward-facing surface 162A. Further, the second jaw 120B may be configured to be rigid, as illustrated. In such embodiments, the second jaw may have a thickness at a similar location as that described above of at least about 2.0 mm, have the same or similar width as the first jaw 120A, and also be made of a heat-treated stainless steel. However, in at least one embodiment, the second jaw 120B may also be made thinner such that its thickness is between about 0.5 mm and about 1.3 mm. In such embodiments, the second jaw 120B may also be flexible and thus both first and second jaws 120A, 120B may be configured to flex when gripping tissue.

In various embodiments, referring now to FIGS. 7 and 8, an end effector 210 of a surgical instrument 200 may comprise compression element(s) 244A extending from a cutting member 240 that may reduce the firing force by including a roller and/or a low-friction material. FIG. 7 shows a schematic diagram of a side view of end effector 210 of surgical instrument 200 gripping and cutting tissue T and FIG. 8 shows a perspective view of a distal portion of the cutting member 240. The surgical instrument 200 may be generally similar to surgical instrument 100 described above with exceptions described below. For example, although not shown, surgical instrument 200 may comprise a handle, such as handle 105 shown in FIG. 1, which may be coupled to a proximal portion of an elongate shaft 208 seen in FIG. 7. Focusing now on FIG. 7, the end effector 210 may likewise be coupled to a distal portion of the elongate shaft 208. In at least one embodiment, the end effector 210 may comprise a first jaw 220A, a second jaw 220B, and a cutting member 240 that is configured to translate with respect to the first and/or second jaws 220A and 220B. Further, the first and second jaws 220A and 220B may be operably coupled together. In at least one embodiment, the jaws 220A and 220B may be pivotably coupled together. For example, a hinge, such as a floating hinge 222, may pivotably couple the first jaw 220A at a jaw pin 226 in a slot 207 formed in the elongate shaft 208, and the second jaw 220B may be fixedly attached to the elongate shaft 208. Alternatively, the hinge 222 may be a fixed pivot hinge (not shown). Also, alternatively, the first jaw 220A may be fixedly attached to the elongate shaft 208. In such embodiments, the first jaw 220A and/or second jaw 220B may comprise a cantilevered beam. Further, in such embodiments, the first jaw 220A and/or the second jaw 220B may be configured to project away from each other and close via a bending action of one or both of the jaws 220A and 220B towards each other. In any event, regardless of how first jaw 220A and second jaw 220B are operably coupled together, they may be configured to rotate and/or deflect with respect to each other between an open position and a closed position when the cutting member 240 translates with respect to the first jaw 220A and/or the second jaw 220B, as discussed below.

As illustrated in FIG. 7, the end effector 210 is shown in a closed configuration, the first jaw 220A of the end effector is shown in an exaggerated flexed or curved configuration while gripping tissue T, and the cutting member 240 is shown in a partially advanced position. A dotted outline 220A' of the first jaw 220A is shown to illustrate an open configuration of the end effector 210. While the cutting member 240 is being advanced between a retracted position and a fully advanced position, as discussed above, the first jaw 220A may be urged to close from an open position to a closed position as shown in FIG. 7. Accordingly, the end effector 210 may further comprise at least one compression element, such as compression elements 244A, extending from the cutting member 240, see FIG. 8. As seen in FIG. 8, the set of compression elements 244A may include first and second compression elements, such as first roller 247 and second roller 249 journaled on shafts or cylindrical projections 251 extending laterally from a body 255 of the cutting member 240 and from a sharp distal edge 253 of the cutting member 240. Further, another compression element, such as inner cam surface 244B of flange 240B, may extend from the opposite side of the cutting member 240 from that of the rollers 247, 249. In such an embodiment, the inner cam surface 244B may function similar to that described above with respect to inner cam surface 144B, see, e.g., FIG. 5.

In various embodiments, the compression elements 244A may be configured to contact the first jaw 220A such that the first jaw 220A rotates with respect to the second jaw 220B when the cutting member 240 translates with respect to the first jaw 220A. In at least one embodiment, the first jaw 220A may comprise an upper first outward-facing surface 262A and the cutting member 240 may be sized and configured to slide along channels in first jaw 220A and/or second jaw 220B (not shown, see however, e.g., channel 142A illustrated in FIGS. 3-4 and discussed above). In such embodiments, the rollers 247, 249 may contact the first jaw's upper surface 262A to urge the first jaw 220A to move from an open position such as that shown by dotted outline 220A' to a closed position as shown in FIG. 7. The inner cam surface 244B of flange 240B may slidably secure the cutting member 240 against a lower outward-facing surface 262B of the second jaw 220B such that the cutting member 240 may translate in a proximal direction PD or in a distal direction DD with respect to the second jaw 220B, but the cutting member 240 may be prevented from moving in a direction transverse to the distal direction DD, toward the first jaw 220A. Accordingly, a localized, high zone of compression, demarcated "HC," may be placed against the tissue T held between the jaws 220A, 220B. The compression element(s) 244A and/or 244B may allow the surgical instrument 200 to reduce the overall forces experienced by the jaws 220A and/or 220B by limiting the area of highest compression HC to the tissue T directly between the distal portions of the compression elements 244A and 244B and around the sharp distal edge 253 of the cutting member 240. As illustrated, the high compression zone HC may be slightly distal to the sharp distal edge 253, thereby allowing tissue to be sealed immediately prior to severing the tissue at the edge 253, for example. Also, at least partially because the area undergoing high compression is limited to the high compression zone HC, the overall compressive forces experienced by the jaws 220A and 220B, when gripping tissue T, may be reduced, thereby also reducing the overall firing force of the surgical instrument 200.

Referring to FIG. 8, as mentioned above, the compression element(s) may comprise a roller or rollers, such as rollers 247, 249. The rollers 247, 249 may allow the cutting member 240 to be advanced in the distal direction DD such that the jaws 220A, 220B are closed on tissue T. However, as the cutting member 240 is advanced, friction between the compression element 244A and the first jaw 220A may resist the travel of the cutting member 240 in the distal direction DD. The rollers 247, 249 may, regardless, roll along the upper surface 262A of the first jaw 220A and thereby reduce the firing force required to advance the cutting member therethrough.

While the compression element(s) may comprise a roller or rollers, the compression element(s) may alternatively or further comprise a low-friction material. In at least one embodiment, the rollers 247, 249, see FIG. 8, may also comprise a low-friction material. For example, the interior of one or both of rollers 247, 249 may be coated with a low-friction material such that the rollers 247, 249 rotate with a reduced coefficient of friction along projections 251. Further, while the rollers 247, 249 are being advanced along surface 262A, see FIG. 7, the frictional forces between the rollers 247, 249 and the surface 262A may increase to the point that one or both of rollers 247 and 249 are prevented from rolling. In such instances where galling and/or sticking of the rollers 247, 249 occurs, for example, the exterior of the rollers 247, 249 may be coated with a low-friction material such that they may also slide along the surface 262A if they are not rolling.

Alternatively, in at least one embodiment, the compression element(s) may include a pad or pads attached to projections extending from the cutting member 240, where the pad is not configured to roll along the surface 262A, but rather to slide along the surface 262A. Further, referring to FIG. 8, the inner cam surface 244B of flange 240B may be coated with a low-friction material such that the frictional forces between the inner cam surface 244B and the lower surface 262B of the second jaw 220B is reduced.

In any event, the firing force required to advance the cutting member in the distal or proximal directions DD, PD may be reduced by one or more of the above embodiments where the compression element or elements comprise a low-friction material.

In various embodiments, the low-friction material may comprise a thermoplastic, including, but not limited to, one or more of the following: nylon, high-density polyethylene, and polytetrafluoroethylene ("PTFE;" sold, for example, under the trade name TEFLON®). The first and second jaws 220A, 220B may be made from heat-treated stainless steel. Accordingly, in various embodiments the static coefficient of friction between the low-friction material of the compression element(s) and the first jaw 220A may be less than or equal to about 0.10. Further, in another embodiment, the static coefficient of friction between the low-friction material and the first jaw may be less than or equal to about 0.07. Additionally, where the compression element(s) comprise PTFE, for example, the static coefficient of friction between the low-friction material and the first jaw may be less than or equal to about 0.05 and/or equal to about 0.04. See, e.g., Kurt Gieck & Reiner Gieck, *Engineering Formulas* §Z.7 (7th ed. 1997).

Referring still to FIG. 7, in at least one embodiment, the cutting member 240 may define a longitudinal axis 225 along which the cutting member 240 may move, and one or both of the jaws 220A, 220B may be precurved to also reduce the firing force. In more detail, in various embodiments, the first jaw 220A may be precurved such that the first jaw 220A curves away from the longitudinal axis 225 when the first jaw 220A is in the open position (represented by dotted outline 220A', for example) and no external load is applied to the first jaw 220A. In other words, the first jaw 220A may be concave when unloaded. In such embodiments, the first jaw may be precurved such that the minimum distance $D_1$ between the first jaw 220A and the second jaw 220B is not less than about 0.006 inches, for example, and/or the maximum distance $D_2$ between the first jaw and the second jaw is not more than about 0.050 inches, for example, when the first jaw is in the closed position as shown in FIG. 7. The minimum distance $D_1$ between the jaws may be configured to occur where the compression element(s) 244A are compressing the tissue T the most, indicated by arrows HC. Further, in at least one embodiment, at least partially because the first jaw 220A is mounted to the elongate shaft 208 by floating hinge 222 and at least partially because the jaw 220A is precurved, the jaw may "rock" with respect to the longitudinal axis 225 as the cutting member 240 and, subsequently, compression element(s) 244A are advanced in a proximal or distal direction PD, DD. This rocking motion may further reduce the required firing force by allowing tissue proximal to the cutting member's sharp distal edge 253 to re-expand after being cut at or near the high compression zone HC.

In at least one embodiment, the first jaw 220A may further be configured to flex when gripping tissue between the first jaw and the second jaw. As described above, such flexing may reduce the required firing force and may result from making the first jaw 220A thin and/or from making the jaw from a flexible material such as a plastic.

Referring now to FIGS. 9 and 10, while various embodiments described above have illustrated an end effector that may include one precurved and/or flexible jaw, in various embodiments, both first and second jaws 320A and 320B of an end effector 310 of a surgical instrument 300 may be precurved and/or flexible. FIG. 9 is a schematic diagram showing a side view of the end effector 310 and FIG. 10 is a perspective view of a distal portion of the cutting member of FIG. 9. The surgical instrument 300 may be generally similar to surgical instruments 100 and/or 200, described above, with exceptions described below. For example, although not shown, surgical instrument 300 may comprise a handle, such as handle 105 shown in FIG. 1, which may be coupled to a proximal portion of an elongate shaft 308 seen in FIG. 9. Focusing now FIG. 9, the end effector 310 may likewise be coupled to a distal portion of the elongate shaft 308. In at least one embodiment, the end effector 310 may comprise a first jaw 320A, a second jaw 320B, and a cutting member 340 that is configured to translate with respect to the first and second jaws 320A and 320B. Further, the first and second jaws 320A and 320B may be operably coupled together. In at least one embodiment, the jaws 320A and 320B may be pivotably coupled together. For example, a hinge, such as a first floating hinge 322A, may pivotably couple the first jaw 320A at a first jaw pin 326A in a first slot 307A formed in the elongate shaft 308, and another hinge, such as second floating hinge 322B, may pivotably couple the second jaw 320B at a second jaw pin 326B in a second slot 307B also formed in the elongate shaft 308. Alternatively, the hinges 322A and 322B may be fixed pivot hinges (not shown). Also, alternatively, the first jaw 320B and the second jaw 320B may be fixedly attached to the elongate shaft 308. In such embodiments, the first jaw 320A and/or second jaw 320B may comprise a cantilevered beam. Further, in such embodiments, the first jaw 320A and/or the second jaw 320B may be configured to project away from each other and close via a bending action of one or both of the jaws 320A and 320B towards each other. In any event, regardless of how first jaw 320A and second jaw 320B are operably coupled together, they may be configured to rotate and/or deflect with respect to each other between an open position and a closed position when the cutting member 340 translates with respect to the first jaw 320A and/or second jaw 320B, as discussed below.

As illustrated in FIG. 9, the end effector 310 is shown in a closed configuration, the first jaw 320A of the end effector is shown in an exaggerated flexed or curved configuration while gripping tissue T, and the cutting member 340 is shown in a partially advanced position. Dotted outlines 320A' and 320B' of the first and second jaws 320A and 320B, respectively, are shown to illustrate an open configuration of the end effector 310. While the cutting member 340 is being advanced between a retracted position and a fully advanced position, as discussed above, one or both of jaws 320A, 320B may be urged to close from an open position or positions to a closed position or positions. Accordingly, the end effector 310 may further comprise at least one compression element, such as first compression elements 344A and second compression elements 344B, extending from the cutting member 340, see FIG. 10. The first set of compression elements 344A may be positioned on one side, e.g., the top side as depicted in FIG. 10, of the cutting member 340, and the second set of compression elements 344B may be positioned on an opposing side, e.g., the bottom side as depicted in FIG. 10, of the cutting member 340. As seen in FIG. 10, the first set of compression elements 344A may include first and second compression elements, such as first roller 347 and second roller 349 journaled on shafts or cylindrical projections 351 extending laterally from a body 355 of the cutting member 340 and from a sharp distal edge 353 of the cutting member 340. The rollers 347 and 349 may be positioned on opposing sides of the cutting member 340. That is, as depicted in FIG. 10, the first roller 347 may be on the right side of the cutting member 340 and the second roller 347 may be on the cutting member's left side.

Similarly, referring still to FIG. 10, the second set of compression elements 344B may include third and fourth compression elements, such as third roller 354 and fourth roller 356 journaled on shafts or cylindrical projections 357 extending laterally from the cutting member's body 355 and from the cutting member's sharp distal edge 353. Like rollers 347 and 349, the rollers 354 and 356 may be positioned on opposing sides of the cutting member 340. That is, as depicted in FIG. 10, the third roller 354 may be on the right side of the cutting member 340 and the second roller 356 may be on the cutting member's left side.

In various embodiments, the compression elements 344A may be configured to contact the first jaw 320A such that the first jaw 320A rotates with respect to the second jaw 320B and/or the elongate shaft 308 when the cutting member 340 translates with respect to the first jaw 320A. Likewise, the compression elements 344B may be configured to contact the second jaw 320B such that the second jaw 320B rotates with respect to the first jaw 320A and/or the elongate shaft 308. In at least one embodiment, the first jaw 320A may comprise an upper first outward-facing surface 362A and the second jaw 320B may comprise a lower outward-facing surface 362B. The cutting member 340 may be sized and configured to slide along channels in first jaw 320A and/or second jaw 320B (not shown, see however, e.g., channels 142A and 142B illustrated in FIG. 3 and discussed above). In such embodiments, the first and second rollers 347 and 349 may contact the first jaw's upper surface 362A to urge the first jaw 320A to move from an open position such as that shown by dotted outline 320A' to a closed position as shown in FIG. 9. Similarly, the third and fourth rollers 354 and 356 may contact the second jaw's lower surface 362B to urge the second jaw 320A to move from an open position such as that shown by dotted outline 320A' to a closed position as shown in FIG. 9. As mentioned above, the cutting member 340 may translate in a proximal direction PD or in a distal direction DD with respect to the first and second jaws 320A and 320B. Accordingly, a localized, high zone of compression, demarcated "HC," may be placed against tissue T held between the jaws 320A, 320B and between compression elements 344A and 344B. The compression elements 344A and/or 344B may allow the surgical instrument 300 to reduce the overall forces experienced by the jaws 320A and/or 320B by limiting the area of highest compression HC to the tissue T directly between the distal portions of the compression elements 344A and 344B and around the sharp distal edge 353 of the cutting member 340. As illustrated, the high compression zone HC may be slightly distal to the sharp distal edge 353, thereby allowing tissue to be sealed immediately prior to severing the tissue at the edge 353, for example. Also, at least partially because the area undergoing high compression is limited to the high compression zone HC, the overall compressive forces experienced by the jaws 320A and 320B, when gripping tissue T, may be reduced, thereby also reducing the overall firing force of the surgical instrument 300.

Referring to FIG. 10, as mentioned above, the compression elements 344A and 344B may comprise rollers, such as rollers 247, 249 and 354, 356, respectively. The rollers 347, 349 and 354, 356 may allow the cutting member 340 to be advanced in the distal direction DD such that the jaws 320A, 320B are closed on tissue T. However, as the cutting member 340 is advanced, friction between the compression elements 344A and 344B may resist the travel of the cutting member 340 in the distal direction DD. The first and second rollers 347, 349 may, regardless, roll along the upper surface 362A of the first jaw 320A, and the third and fourth rollers 354, 356 may roll along the lower surface 362B of the second jaw 320B to thereby reduce the firing force required to advance the cutting member therethrough.

While the compression element (s) may comprise a roller or rollers, the compression element(s) may alternatively or further comprise a low-friction material. In at least one embodiment, the rollers 247, 249 and 354, 356, see FIG. 10, may also comprise a low-friction material. For example, the interior of one or more of rollers 247, 249, 354, and 356 may be coated with a low-friction material such that the rollers 247, 249 354, and 356 collectively rotate with a reduced coefficient of friction along projections 351 and/or 357. Further, while the first and second rollers 247, 249 are being advanced along upper surface 362A and the third and fourth rollers 354, 356 are being advanced along lower surface 362B, see FIG. 9, the frictional forces between the rollers 247, 249 and 354, 356 and the surfaces 362A and 362B, respectively, may increase to the point that one or more of rollers 347, 349, 354, and 356 are prevented from rolling. In such instances where galling and/or sticking of the rollers occurs, the exterior of the rollers 247, 249, 354, and/or 356 may be coated with a low-friction material such that they may also slide along the surfaces 362A and 362B if they are not rolling.

Alternatively, in at least one embodiment, the compression element(s) may include a pad or pads attached to projections extending from the cutting member 340, where the pad or pads are not configured to roll along the surfaces 362A and/or 362B, but rather to slide along the surfaces 362A and/or 362B.

In any event, the firing force required to advance the cutting member 340 in the distal or proximal directions DD, PD may be reduced by one or more of the above embodiments where one or more of the compression elements comprise a low-friction material.

In various embodiments, the low-friction material may comprise a thermoplastic, including, but not limited to, one or more of the following: nylon, high-density polyethylene, and polytetrafluoroethylene ("PTFE;" sold, for example, under the trade name TEFLON®). The first and second jaws 320A, 320B may be made from heat-treated stainless steel. Accordingly, in various embodiments the static coefficient of friction between the low-friction material of the compression element(s) and the first jaw 320A may be less than or equal to about 0.10. Further, in another embodiment, the static coefficient of friction between the low-friction material and the first jaw may be less than or equal to about 0.07. Additionally, where the compression element(s) comprise PTFE, for example, the static coefficient of friction between the low-friction material and the first jaw may be less than or equal to about 0.05 and/or equal to about 0.04. See, e.g., Kurt Gieck & Reiner Gieck, *Engineering Formulas* §Z.7 (7th ed. 1997).

Referring back to FIG. 9, in at least one embodiment, the cutting member 340 may also define a longitudinal axis 325 along which the cutting member 340 may move, and one or both of the jaws 320A, 320B may be precurved to also reduce the firing force. In more detail, in various embodiments, the first jaw 320A may be precurved such that the first jaw 320A curves away from the longitudinal axis 325 when the first jaw 320A is in the open position (represented by dotted outline 320A', for example) and no external load is applied to the first jaw 320B. Further, the second jaw 320B may also be precurved such that the second jaw 320B curves away from the longitudinal axis 325 when the second jaw 320B is in the open position (represented by dotted outline 320B', for example) and no external load is applied to the second jaw 320B. In other words, the first jaw 320A and/or the second jaw 320B may be concave when unloaded.

In at least one embodiment, at least partially because the jaws 320A and 320B are mounted to the elongate shaft 308 by floating hinge 322 and at least partially because the jaw 320A is precurved, the jaws may each independently "rock" with respect to the longitudinal axis 325 as the cutting member 340 and, subsequently, compression elements 344A and 344B are advanced in a proximal or distal direction PD, DD. These rocking motions may further reduce the required firing force by allowing tissue proximal to the cutting member's sharp distal edge 353 to re-expand after being cut at or near the high compression zone HC.

In at least one embodiment, the first jaw 320A and/or second jaw 320B may further be configured to flex when gripping tissue between the first jaw 320A and the second jaw 320B. As described above, such flexing may reduce the required firing force and may result from making either or both of jaws 320A and 320B thin and/or from making the jaw from a flexible material such as a plastic.

Thus, in various embodiments, the overall force required to advance a cutting member, close jaws, and/or otherwise operate an end effector of a surgical instrument may be reduced. Further, in various embodiments, a larger range of tissue types and thicknesses may be accommodated than that currently possible with other surgical devices. Moreover, in various embodiments, the target tissue being griped by a surgical instrument may undergo high compressive forces nearest a cutting edge of the instrument and reduced compressive forces away from the cutting edge.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A surgical instrument, comprising:
    an end effector comprising:
        a first flexible jaw defining a longitudinal axis and a channel;
        a second jaw, wherein the first flexible jaw and the second jaw are operably coupled together;

a cutting member including a distal end, wherein the cutting member is sized and configured to fit at least partially within the channel, the cutting member configured to translate along the channel between a retracted position and a fully advanced position, wherein the first flexible jaw has a thickness less than or equal to 1.3 mm in a direction perpendicular to the longitudinal axis and at a plane that transects the channel at the distal end of the cutting member when the cutting member is between the retracted position and the fully advanced position; and at least one compression element extending distally from the cutting member, wherein the at least one compression element is configured to cause the first flexible jaw to rotate with respect to the second jaw from an open position to a closed position when the cutting member translates with respect to the first flexible jaw beyond the retracted position, wherein the at least one compression element comprises a roller, and wherein the roller is configured to be advanced ahead of the cutting member as the cutting member translates to the fully advanced position.

2. The surgical instrument of claim 1, wherein the thickness of the first flexible jaw is greater than or equal to 0.5 mm and wherein the first flexible jaw has a width between and including 2 mm to 15 mm.

3. The surgical instrument of claim 1, wherein the first flexible jaw and the second jaw are pivotably coupled together.

4. A surgical instrument, comprising:
an end effector coupled comprising:
a first jaw;
a second jaw, wherein the first jaw and the second jaw are operably coupled together;
a cutting member configured to translate with respect to the first jaw and the second jaw; and
at least one compression element extending distally from the cutting member, wherein the at least one compression element is configured to contact the first jaw such that the first jaw rotates with respect to the second jaw when the cutting member translates with respect to the first jaw, wherein the at least one compression element comprises a roller and a low-friction material, wherein the static coefficient of friction between the low-friction material and the first jaw is less than or equal to 0.10, wherein the at least one compression element comprises a rolling member, and wherein the rolling member is configured to be advanced ahead of the cutting member as the cutting member translates distally with respect to the first jaw.

5. The surgical instrument of claim 4, wherein the static coefficient of friction between the low-friction material and the first jaw is less than or equal to 0.07.

6. The surgical instrument of claim 4, wherein the static coefficient of friction between the low-friction material and the first jaw is less than or equal to 0.05.

7. The surgical instrument of claim 4, wherein the low-friction material comprises a thermoplastic.

8. The surgical instrument of claim 7, wherein the thermoplastic is one or more of nylon, high-density polyethylene, and polytetrafluoroethylene.

9. The surgical instrument of claim 4, wherein the first jaw and the second jaw are pivotably coupled together.

10. A surgical instrument, comprising:
an end effector comprising:
a first jaw;
a second jaw, wherein the first jaw and the second jaw are operably coupled together;
a cutting member configured to translate with respect to the first jaw between a retracted position and a fully advanced position, the cutting member defining a longitudinal axis; and
at least one compression element extending distally from the cutting member, wherein the at least one compression element is configured to contact the first jaw such that the first jaw rotates with respect to the second jaw between an open position and a closed position when the cutting member translates with respect to the first jaw, wherein the first jaw is precurved such that the first jaw curves away from the longitudinal axis when the first jaw is in the open position and no external load is applied to the first jaw, wherein the at least one compression element comprises a rotatable member, and wherein the rotatable member is configured to be advanced ahead of the cutting member as the cutting member translates to the fully advanced position.

11. The surgical instrument of claim 10, wherein the first jaw is mounted to a floating hinge.

12. The surgical instrument of claim 10, wherein the first jaw is configured to flex when gripping tissue between the first jaw and the second jaw.

13. The surgical instrument of claim 12, wherein the first jaw is mounted to a fixed pivot hinge.

14. The surgical instrument of claim 10, wherein the first jaw is precurved such that the minimum distance between the first jaw and the second jaw is not less than 0.006 inches and the maximum distance between the first jaw and the second jaw is not more than 0.050 inches when the first jaw is in the closed position.

15. The surgical instrument of claim 10, wherein the cutting member is configured to translate with respect to the second jaw between the retracted position and the fully advanced position, wherein the at least one compression element is configured to cause the second jaw to rotate with respect to the first jaw between an open position and a closed position when the cutting member translates with respect to the second jaw, wherein the second jaw is precurved such that the second jaw curves away from the cutting member's longitudinal axis when the second jaw is in the open position and no external load is applied to the second jaw.

16. The surgical instrument of claim 15, wherein the second jaw is mounted to a floating hinge.

17. The surgical instrument of claim 15, wherein the second jaw is configured to flex when gripping tissue between the first jaw and the second jaw.

18. The surgical instrument of claim 17, wherein the second jaw is mounted to a fixed pivot hinge.

19. The surgical instrument of claim 10, wherein the rotatable member is journaled on a shaft extending from the cutting member.

20. The surgical instrument of claim 10, wherein the at least one compression element comprises a first compression element and a second compression element, wherein the first and second compression elements are positioned on opposing sides of the cutting member.

21. The surgical instrument of claim 20, wherein the first and second compression elements are configured to contact the first jaw.

22. The surgical instrument of claim 10, wherein the at least one compression element comprises a first compression element, a second compression element, a third compression element, and a forth compression element, wherein the first compression element and the second compression element are configured to contact the first jaw, and wherein the third compression element and the fourth compression element are configured to contact the second jaw.

23. The surgical instrument of claim 10, wherein the first jaw and the second jaw are pivotably coupled together.

* * * * *